(12) United States Patent
Liang et al.

(10) Patent No.: US 10,100,036 B2
(45) Date of Patent: Oct. 16, 2018

(54) LAPPACONITINE AZA-CINNAMIC ACID DERIVATIVES WITH ANTI-TUMOR ACTIVITIES AND A METHOD OF PREPARING THE SAME

(71) Applicants: Chengyuan Liang, Xi'an (CN); Minyi Jia, Xi'an (CN); Xingke Ju, Xi'an (CN); Lei Tian, Xi'an (CN); Danni Tian, Xi'an (CN); Shunjun Ding, Xi'an (CN)

(72) Inventors: Chengyuan Liang, Xi'an (CN); Minyi Jia, Xi'an (CN); Xingke Ju, Xi'an (CN); Lei Tian, Xi'an (CN); Danni Tian, Xi'an (CN); Shunjun Ding, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 15/713,934

(22) Filed: Sep. 25, 2017

(65) Prior Publication Data

US 2018/0093966 A1 Apr. 5, 2018

(30) Foreign Application Priority Data

Sep. 30, 2016 (CN) .......................... 2016 1 0873469
Jul. 21, 2017 (CN) .......................... 2017 1 0598889

(51) Int. Cl.
*C07D 401/12* (2006.01)

(52) U.S. Cl.
CPC .................. *C07D 401/12* (2013.01)

(58) Field of Classification Search
CPC .................................................... C07D 401/12
See application file for complete search history.

(56) References Cited

PUBLICATIONS

Romanov et al., New Acyl Derivatives of N-Deacetyllappaconitine; Chemistry of Natural Compounds, vol. 44, No. 3, 2008, pp. 346-351.*

* cited by examiner

*Primary Examiner* — Alexander R Pagano
*Assistant Examiner* — Ebenezer O Sackey

(57) ABSTRACT

A lappaconitine aza-cinnamic acid derivative having the following formula (I):

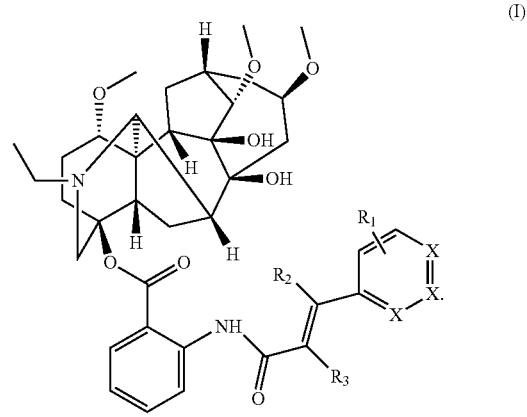

X is C or N, and $R_1$, $R_2$, and $R_3$ are independently H or lower alkyl. A method of preparing the lappaconitine aza-cinnamic acid derivative of formula (I) is also disclosed.

6 Claims, No Drawings

LAPPACONITINE AZA-CINNAMIC ACID DERIVATIVES WITH ANTI-TUMOR ACTIVITIES AND A METHOD OF PREPARING THE SAME

The present invention claims priority to Chinese Patent Application No. 201710598889.1, filed on Jul. 21, 2017, which claims priority to Chinese Patent Application No. 201610873469.5, filed on Sep. 30, 2016, both of which are incorporated by reference for all purposes as if fully set forth herein.

FIELD OF THE INVENTION

The present invention relates to the field of medicinal chemistry, and in particular, to lappaconitine aza-cinnamic acid derivatives having antitumor activities and a method of preparing the same

BACKGROUND OF THE INVENTION

Cancer has become a serious threat to human health. Researchers are pursuing effective, safe, and low-toxicity small molecular anti-tumor drugs. With the development of medicinal chemistry, research on natural products with anti-tumor activities and the derivatives of these products became an important trend.

Lappaconitine ((1α, 14α, 16β)-20-ethyl-1,14,16-trimethoxycephin-4,8,9-triol 4-[2-(acetylamino)]benzoate, formula (II)) is an alkaloid isolated from the roots of *Aconitumsinomotanum Nakai*. (Advanced Chinese Plant Illustration, Vol. I, Institute of Botany, Chinese Academy of Sciences, Science Press, Beijing, 1992, page 688). Pharmacological experiments show that lappaconitine has a strong central analgesic effect, antipyretic, and local anesthesia effect. Toxicity experiments show that lappaconitine has no damage to the various organizations and no teratogenic effect.

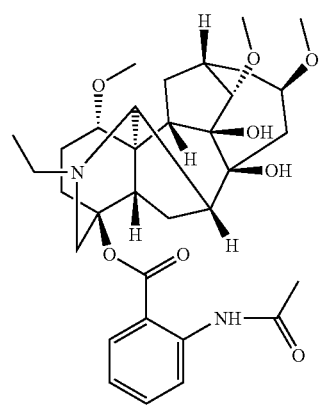

(II)

Cinnamic acid is a natural aromatic fatty acid that is widely found in propolis, coffee, fruit and wine. Cinnamic acid has a wide range of pharmacological properties, such as anti-cancer, anti-oxidation, and antibacterial.

Recently, nitrogen-containing heterocyclic compounds and their derivatives have been used in the fields of medicine, pesticide and fuel. In pharmaceuticals, nitrogen-containing heterocyclic compounds are widely used, from penicillin to the present fourth-generation cephalosporins, antihypertensive drugs reserpine, pyrimidine antagonists antitumor with activity, barbiturates sedative hypnotic drugs, and synthetic analgesic drugs.

Cinnamic acid, aza-cinnamic acid and their derivatives have antitumor activities. As one new drug research and development strategy, they can be used as lead compounds for further research to obtain candidate compounds with better efficacy. One example is histone deacetylase inhibitor (HDI) inhibitor, Chidamide (approved in 2014), which was inspired by the introduction of aza-cinnamic acid and its derivatives in the compound design.

There remains a need for effective and safe small molecular anti-tumor drugs. There is also no report of lappaconitine aza-cinnamic acid derivatives.

SUMMARY OF THE INVENTION

In one embodiment, the present invention provides a lappaconitine aza-cinnamic acid derivative having the following formula (I):

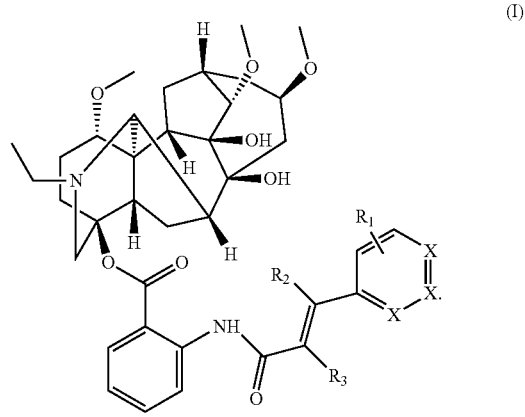

(I)

In formula (I), X is C or N, and $R_1$, $R_2$, and $R_3$ are independently H or lower alkyl.

In another embodiment, the lappaconitine aza-cinnamic acid derivative is

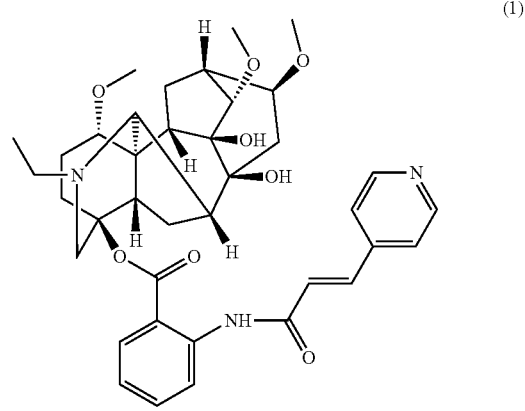

(1)

-continued
(2)
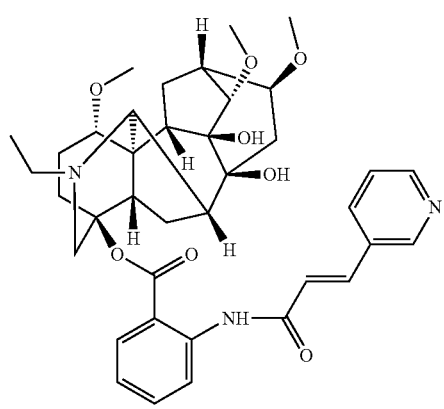
(3)
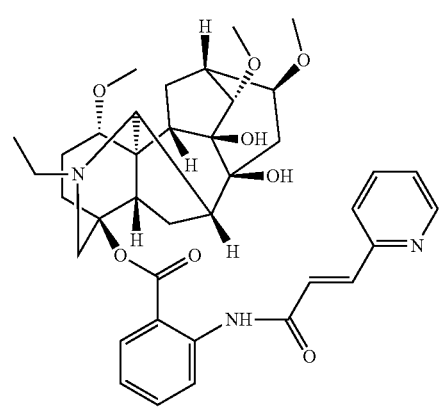
(4)
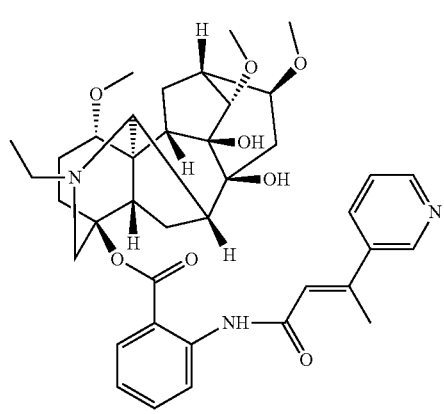
(5)
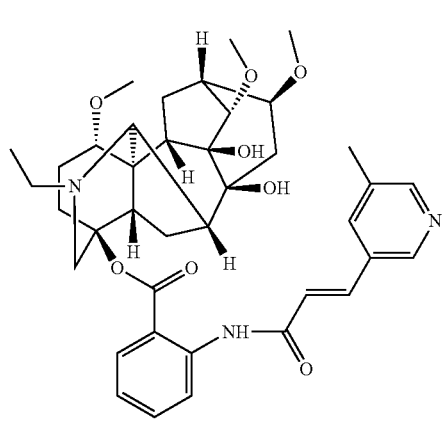
-continued
(6)
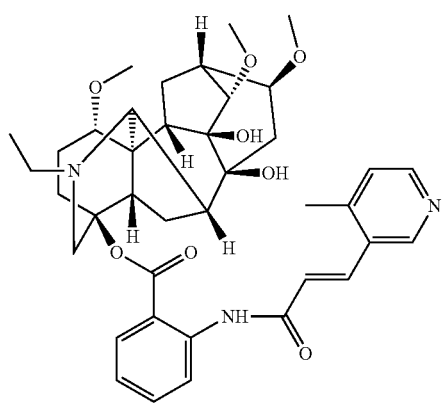
(7)
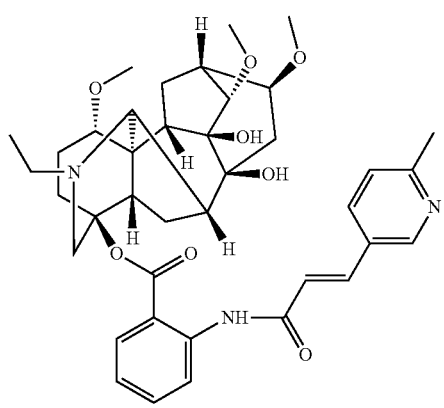
(8)
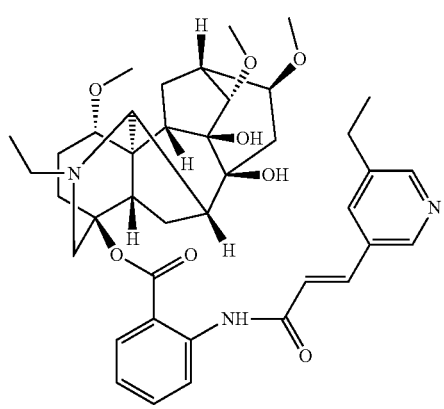
(9)
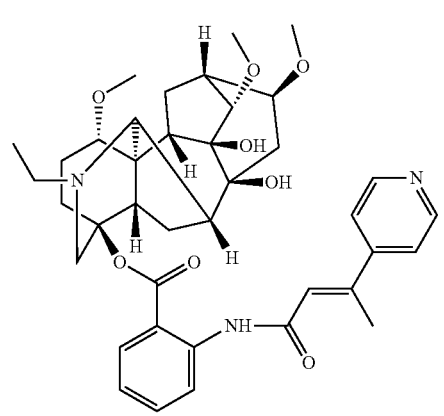

(10)
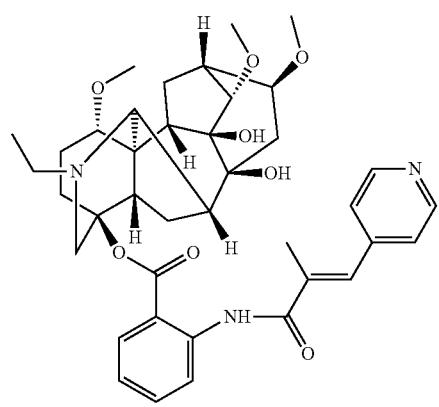
(11)
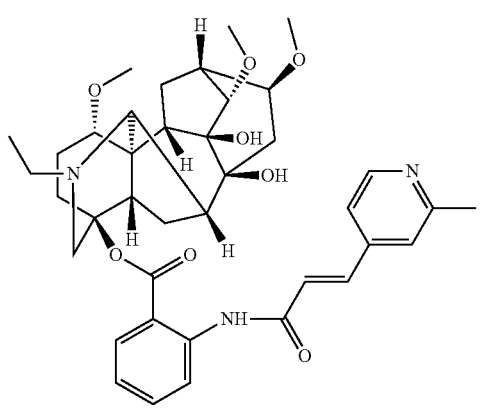
(12)
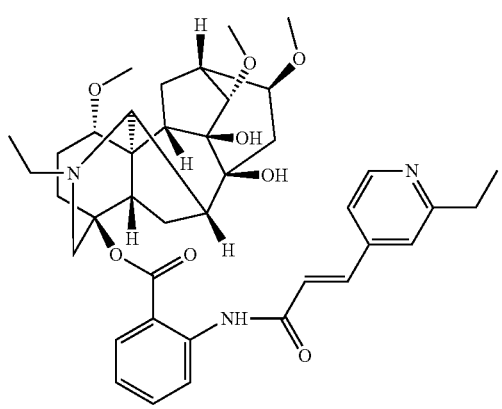
(13)
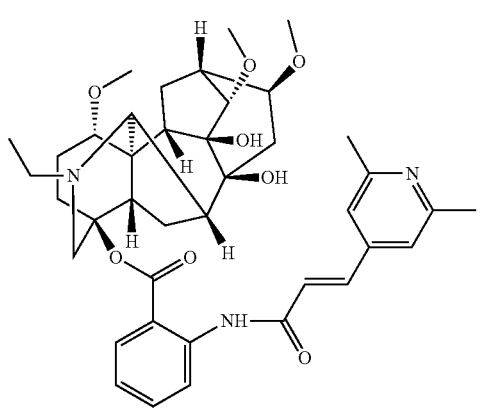
(14)
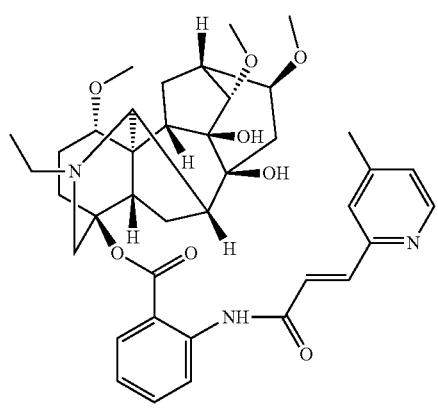
(15)
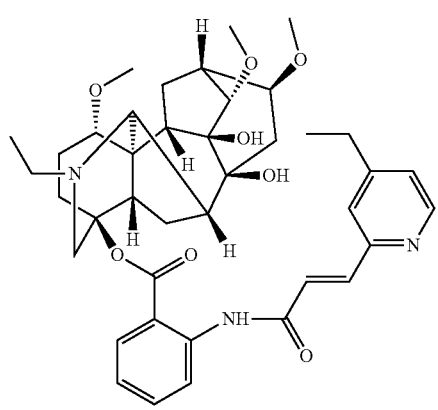
(16)
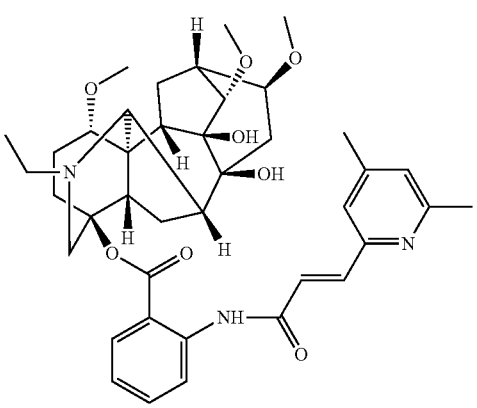
(17)
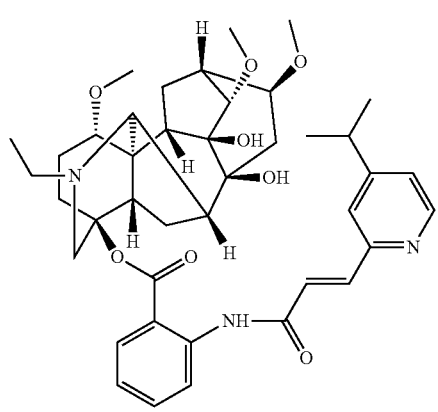

-continued (18)

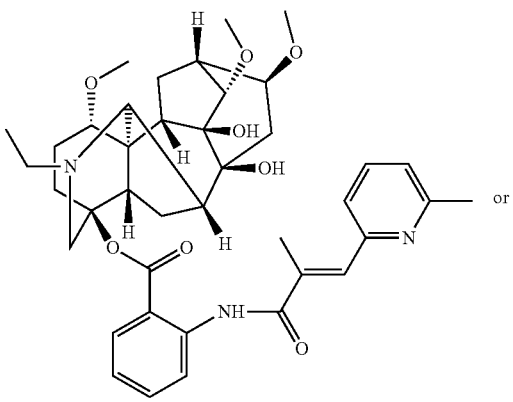

or (19)

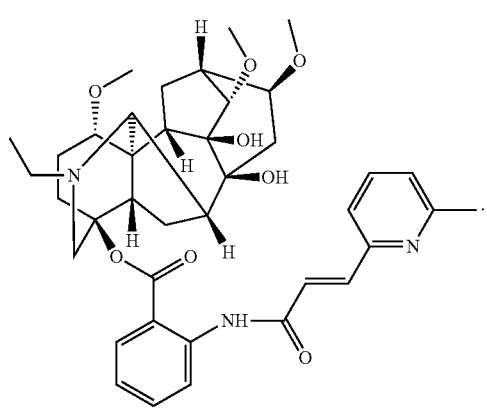

In another embodiment, the present invention provides a method of preparing lappaconitine Aza-cinnamic acid derivatives with antitumor activities. The method includes: reacting a compound of formula (II):

(II)

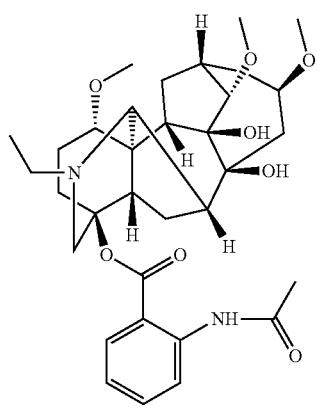

with HCl to obtain a compound of formula (III):

(III)

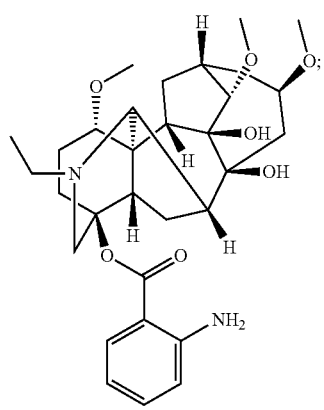

and reacting the compound of formula (III) with a compound of formula (IV):

(IV)

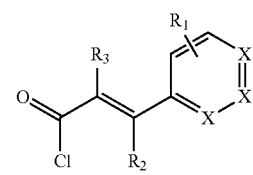

to obtain a lappaconitine aza-cinnamic acid derivative having the following formula (I):

(I)

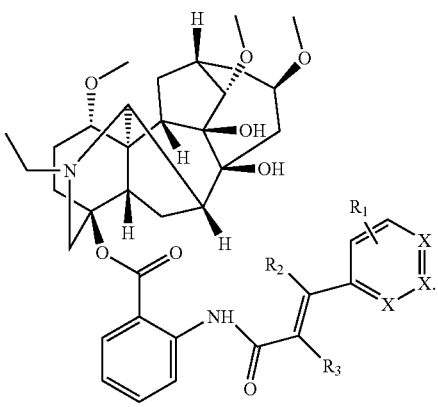

In formulas (I), (II), (III), and (IV), X is C or N, and $R_1$, $R_2$, and $R_3$ are independently H or lower alkyl.

In another embodiment, the compound of formula (II) reacts with 2% HCl in ethanol in a molar ratio of 1:5.

In another embodiment, the compound of formula (III) reacts with the compound of formula (IV) in DMF in a molar ratio of 1:1.1-12 with DCC as a catalyst.

In another embodiment, the compound of formula (III) reacts with the compound of formula (IV) at 50° C.-90° C.

In another embodiment, the compound of formula (III) reacts with the compound of formula (IV) at 60° C.-80° C.

In another embodiment, the present invention provides a method of using the lappaconitine aza-cinnamic acid derivative of formula (I) in antitumor drug research, development, and application.

In another embodiment, the present invention provides a method of using the lappaconitine aza-cinnamic acid derivative of formula (I) in treating human prostate cancer, stomach cancer, lung cancer, breast cancer, or liver cancer.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention.

It is an object of the present invention to provide compounds with anti-tumor activities and a method of preparing the same. The method has the advantages of low-cost and abundant raw material, low production cost, high operational safety, mild conditions, high yields, suitable for industrial production. The lappaconitine aza-cinnamic acid derivatives can be used in cancer research and to treat various cancers.

To achieve the above objects, the technical solution adopted by the present invention is described in details below.

A lappaconitine aza-cinnamic acid derivative with anti-tumor activities has the following formula (I):

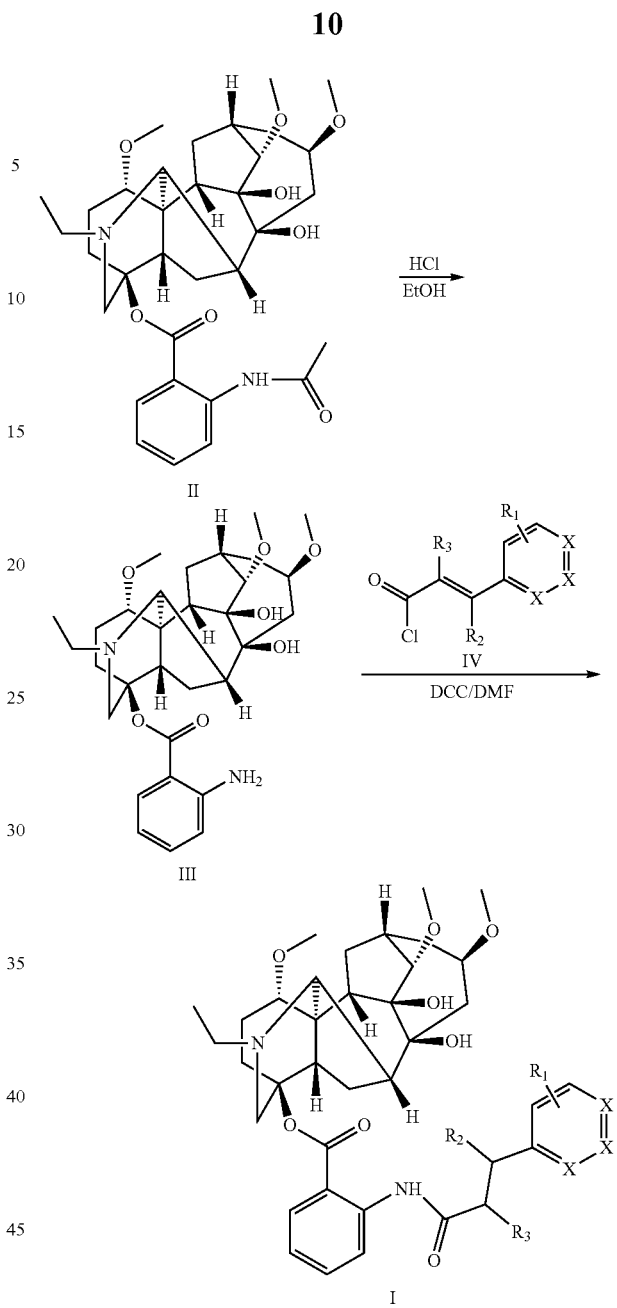

In formula (I), X is C or N, and $R_1$, $R_2$, and $R_3$ are independently H or lower alkyl. The term "lower alkyl" refers to a monovalent straight or branched chain, saturated aliphatic hydrocarbon radical having 1-8 carbon atoms. For example, alkyl refers to any of the hexyl alkyl and pentyl alkyl isomers as well as n-, iso-, sec- and t-butyl, n- and iso-propyl, ethyl, or methyl.

A method of preparing a lappaconitine aza-cinnamic acid derivative of formula (I) using lappaconitine (formula (II)), aza-cinnamic acid and its derivatives (formula (IV)) as starting materials and DMF (dimethylformamide) as reaction solvent. The reaction scheme is as follows:

In formulas (I), (II), (IIII), and (IV), X is C or N, and $R_1$, $R_2$, and $R_3$ are independently H or lower alkyl.

Details of reaction steps are as follows:

1) Lappaconitine and 2% (wt) HCl were added to a reactor in a molar ratio of 1:5. Ethanol was used as reaction solvent. The reaction mixture was stirred at room temperature. The reaction was monitored with TLC (Thin Layer Chromatograph) until completion. After reaction is complete, reaction solvent was removed under vacuum to obtain an intermediate (formula (III)).

2) Aza-cinnamic acid or its derivative was added to the intermediate of step 1) in a molar ratio of 1:1 to 1:2. DMF was used as reaction solvent, and DCC (N,N'-dicyclohexylcarbodiimide) was used as a catalyst. The reaction mixture was stirred and heated at 50° C.-90° C. The reaction was monitored with TLC until completion.

3) After reaction in step 2) is complete, the reaction was quenched with water, and the mixture was extracted with DCM (dichloromethane) to obtain a crude product.

4) The crude product was purified by flash chromatograph to obtain desired product (formula (I)).

In step 1), 2% HCl was a catalyst.

In step 2), the molar ratio of lappaconitine and aza-cinnamic acid or its derivative is 1:1.2 to 1:1.5.

In step 2), DMF was a reaction solvent.

In step 3), the reaction temperature is preferably 60° C.-80° C.

The lappaconitine aza-cinnamic acid derivative of formula (I) is preferably:

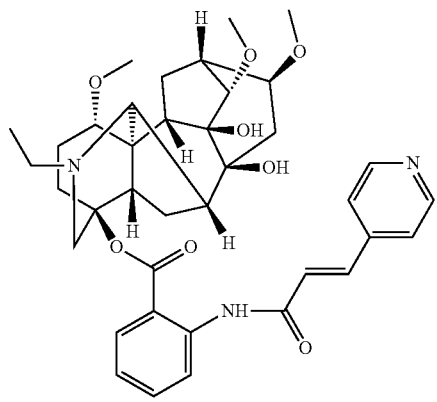

(1)

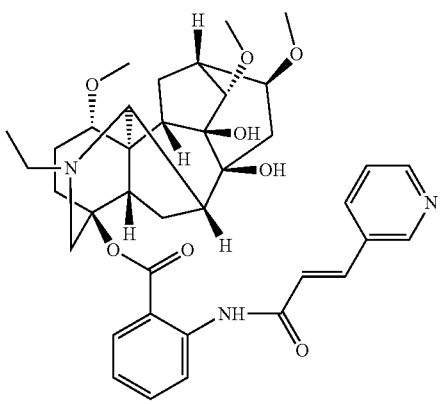

(2)

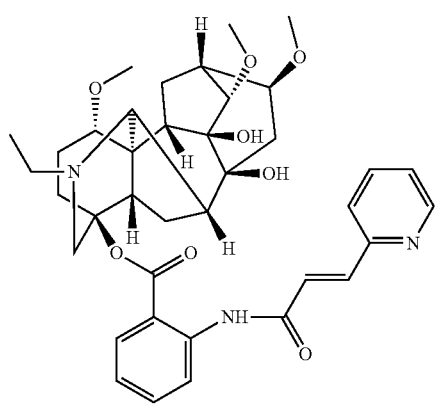

(3)

-continued

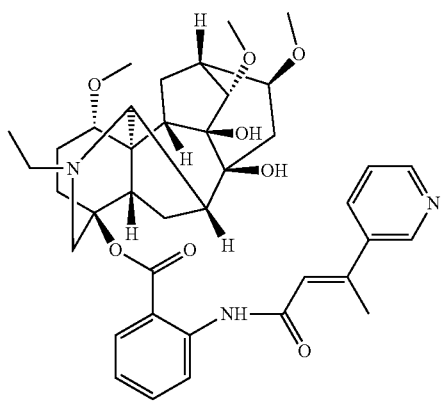

(4)

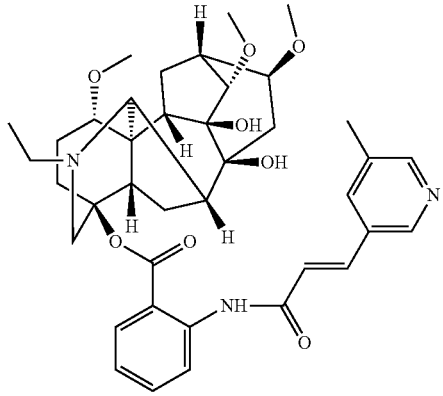

(5)

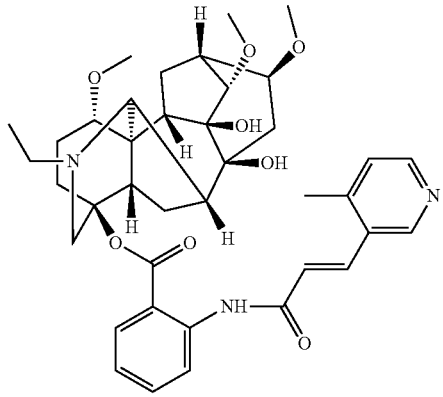

(6)

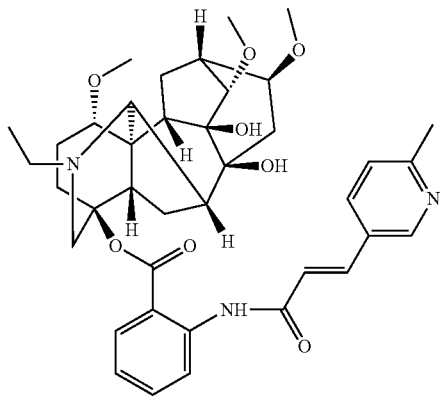

(7)

-continued
(8)
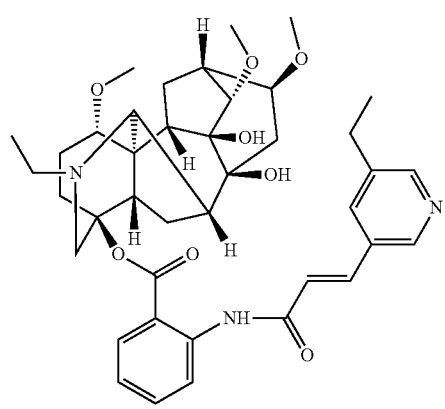
(9)
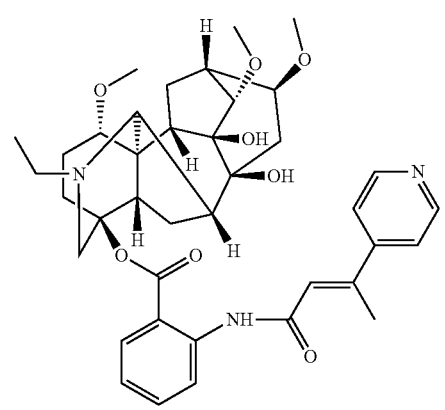
(10)
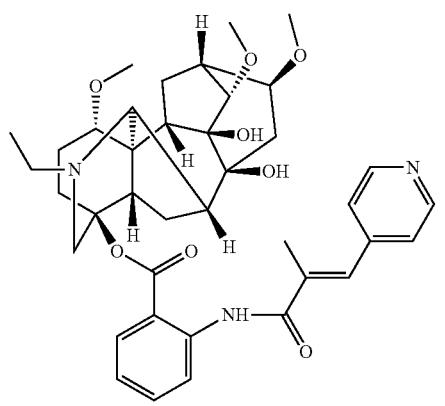
(11)
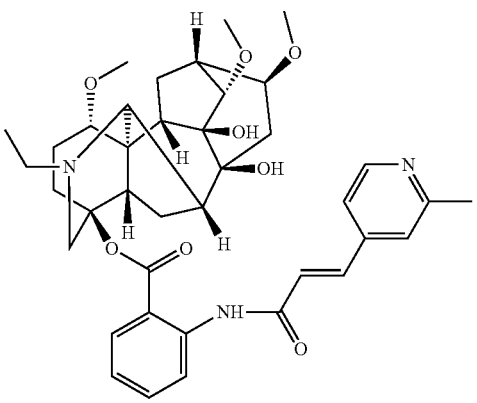
-continued
(12)
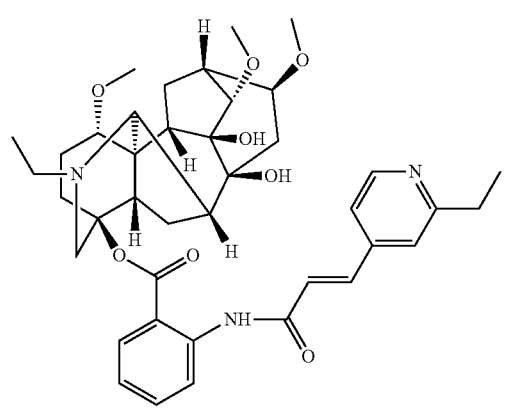
(13)
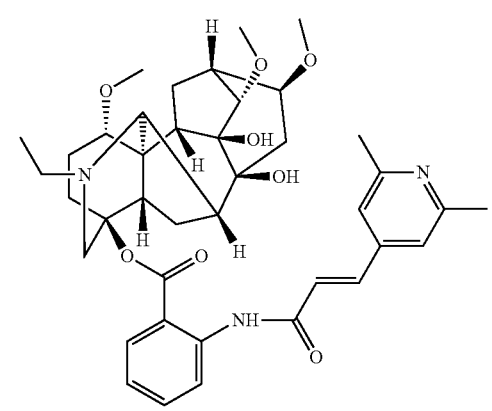
(14)
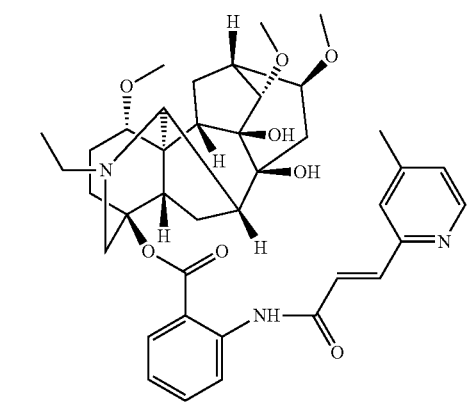
(15)
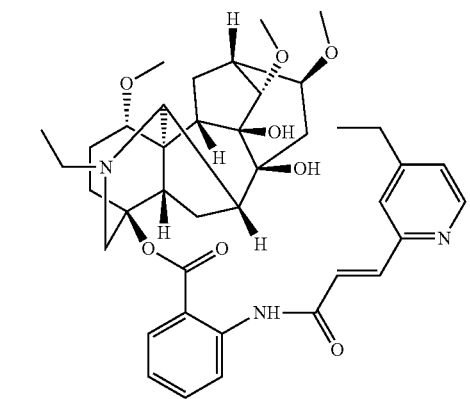

(16)

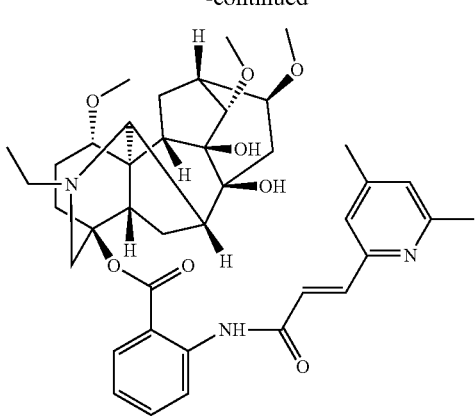

(17)

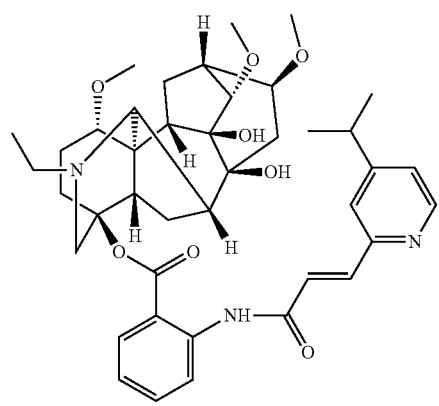

(18)

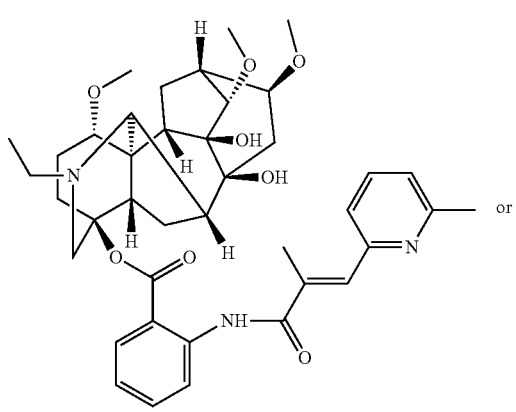

or (19)

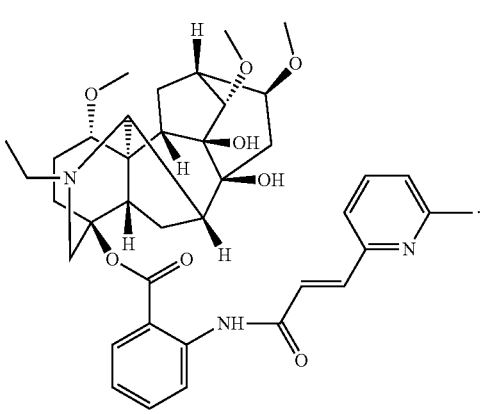

The above-described one-pot synthesis method of lappaconitine aza-cinnamic acid derivatives has the advantages of low-cost and abundant raw material, low production cost, high operational safety, mild conditions, high yields, suitable for industrial production. The lappaconitine aza-cinnamic acid derivatives can be used in cancer research and to treat various cancers.

The present invention will now be described in further detail with reference to specific inventive examples below, but the present invention is not limited to the following examples.

Example 1

Lappaconitine and 4-Aza-Cinnamic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 17.20 mg of 4-aza-cinnamic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (29.64 mg; overall yield: 54.69%). The desired product has the following structure and characteristics.

(1)

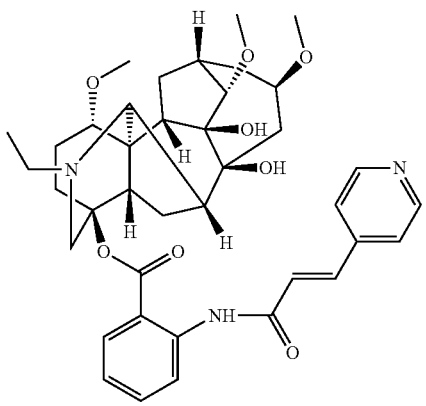

White crystalline powder. M.P. 182-184° C. $^1$H-NMR (400 MHz, DMSO-$d_6$) δ: 10.12 (1H, s), 8.54 (2H, d), 8.30 (4H, m), 7.47 (2H, d), 7.35 (1H, s), 7.19 (1H, s), 3.65 (2H, s), 3.30 (9H, s), 2.85 (1H, d), 2.78 (1H, q), 2.77 (1H, t), 2.75 (2H, s), 2.54 (2H, d), 2.50 (2H, s), 2.40 (2H, q), 2.36 (1H, m), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.02 (3H, t); $^{13}$C-NMR (100 MHz, DMSO-$d_6$) δ: 168.0, 167.1, 149.6, 144.5, 141.4, 140.3, 133.2, 130.1, 125.4, 124.2, 123.0, 119.2, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.0, 13.6; MS (ESI) for [M+H]$^+$: 674.3.

Example 2

Lappaconitine and 3-Aza-Cinnamic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 17.20 mg of 3-aza-cinnamic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (30.04 mg; overall yield: 55.42%). The desired product has the following structure and characteristics.

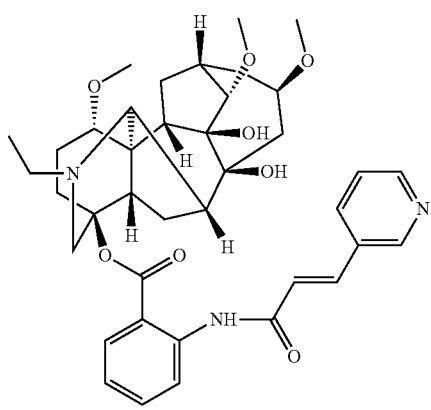

(2)

White crystalline powder. M.P. 182-184° C. $^1$H-NMR (400 MHz, DMSO-d6) δ: 10.12 (1H, s), 8.84 (2H, s), 8.33 (1H, d), 8.30 (4H, m), 7.98 (1H, d), 7.71 (1H, s), 7.55 (1H, t), 6.89 (1H, s), 3.65 (2H, s), 3.30 (9H, s), 2.85 (1H, d), 2.78 (1H, q), 2.77 (1H, t), 2.75 (2H, s), 2.54 (2H, d), 2.50 (2H, s), 2.40 (2H, q), 2.36 (1H, m), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.02 (3H, t); $^{13}$C-NMR (100 MHz, DMSO-d$_6$) δ: 168.0, 167.1, 149.5, 148.1, 140.3, 136.6, 133.2, 132.5, 130.1, 129.6, 124.8, 124.2, 123.8, 119.2, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.0, 13.6; MS (ESI) for [M+H]$^+$: 674.3.

Example 3

Lappaconitine and 2-Aza-Cinnamic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 17.20 mg of 2-aza-cinnamic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (28.96 mg; overall yield: 53.43%). The desired product has the following structure and characteristics.

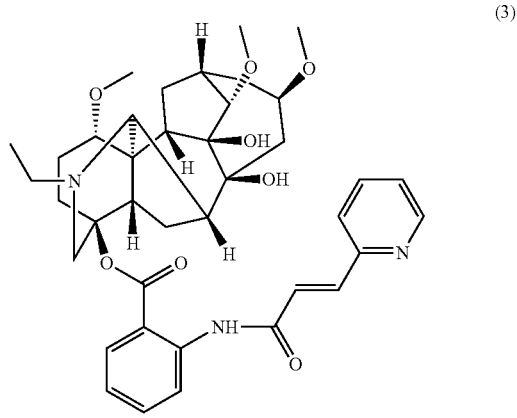 [SMILES: CCN1C[C@]2(OC(=O)c3ccccc3NC(=O)/C=C/c3ccccn3)CC[C@H](OC)[C@]34C1[C@@H](C[C@H]23)[C@@]1(O)C[C@H](OC)C[C@H]2C[C@@H]4[C@]1(O)[C@H]2OC]

(3)

White crystalline powder. M.P. 182-184° C. $^1$H-NMR (400 MHz, DMSO-d$_6$) δ: 10.12 (1H, s), 8.45 (1H, d), 8.30 (4H, m), 7.76 (1H, s), 7.50 (1H, s), 7.43 (1H, d), 7.41 (1H, t), 7.29 (1H, t), 3.65 (2H, s), 3.30 (9H, s), 2.85 (1H, d), 2.78 (1H, q), 2.77 (1H, t), 2.75 (2H, s), 2.54 (2H, d), 2.50 (2H, s), 2.40 (2H, q), 2.36 (1H, m), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.02 (3H, t); $^{13}$C-NMR (100 MHz, DMSO-d$_6$) δ: 168.0, 167.1, 154.7, 148.8, 140.3, 138.2, 137.0, 133.2, 130.1, 124.5, 124.3, 124.2, 122.7, 119.2, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.0, 13.6; MS (ESI) for [M+H]$^+$: 674.3.

Example 4

Lappaconitine and 3-(3-pyridyl)-3-methacrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 18.64 mg of 3-(3-pyridyl)-3-methacrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (27.96 mg; overall yield: 47.53%). The desired product has the following structure and characteristics.

(4)

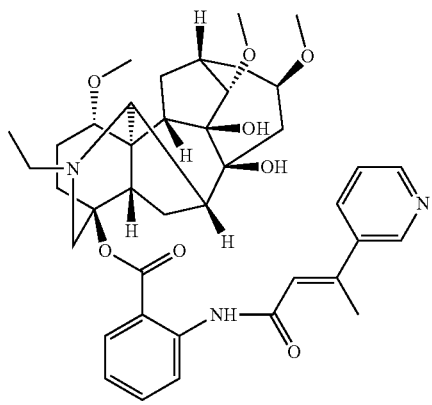

White crystalline powder. M.P. 182-184° C. $^1$H-NMR (400 MHz, DMSO-$d_6$) δ: 10.12 (1H, s), 8.47 (1H, s), 8.33 (1H, d), 8.30 (4H, m), 7.70 (1H, d), 7.29 (1H, t), 6.56 (1H, s), 3.65 (2H, s), 3.30 (9H, s), 2.85 (1H, d), 2.78 (1H, q), 2.77 (1H, t), 2.75 (2H, s), 2.54 (2H, d), 2.50 (2H, s), 2.42 (3H, s), 2.40 (2H, q), 2.36 (1H, m), 2.13 (4H, m), 1.99 (1H, t), 1.95 (2H, t), 1.88 (4H, m), 1.8 (2H, d), 1.73 (1H, t), 1.70 (4H, m), 1.55 (2H, d), 1.48 (1H, s), 1.45 (2H, q), 1.02 (3H, t); $^{13}$C-NMR (100 MHz, DMSO-$d_6$) δ: 167.1, 166.0, 154.2, 153.0, 149.5, 140.3, 133.9, 133.2, 130.1, 124.2, 123.8, 121.8, 119.2, 118.4, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.0, 13.6, 13.0; MS (ESI) for [M+H]$^+$: 688.8.

Example 5

Lappaconitine and 3-(5-methyl-3-pyridyl) Acrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 18.64 mg of 3-(5-methyl-3-pyridyl) acrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (27.54 mg; overall yield: 47.53%). The desired product has the following structure and characteristics.

(5)

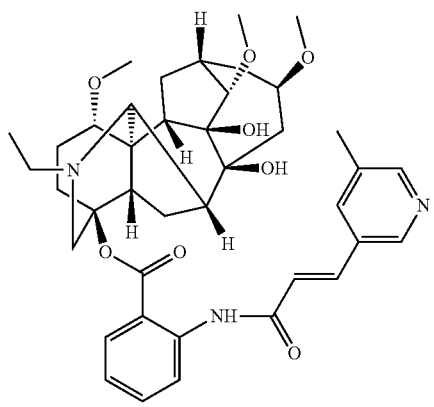

White crystalline powder. M.P. 182-184° C. $^1$H-NMR (400 MHz, DMSO-$d_6$) δ: 10.12 (1H, s), 8.82 (1H, s), 8.30 (4H, m), 8.29 (1H, s), 7.73 (1H, s), 7.71 (1H, s), 6.89 (1H, s), 3.65 (2H, s), 3.30 (9H, s), 2.85 (1H, d), 2.78 (1H, q), 2.77 (1H, t), 2.75 (2H, s), 2.54 (2H, d), 2.50 (2H, s), 2.40 (2H, q), 2.36 (1H, m), 2.31 (3H, s), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.02 (3H, t); $^{13}$C-NMR (100 MHz, DMSO-$d_6$) δ: 168.0, 167.1, 166.0, 151.2, 150.0, 140.3, 16.6, 133.9, 132.9, 130.1, 129.0, 124.8, 124.2, 119.2, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.0, 18.4, 13.6; MS (ESI) for [M+H]$^+$: 688.8.

Example 6

Lappaconitine and 3-(6-methyl-3-pyridyl) Acrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 18.64 mg of 3-(6-methyl-3-pyridyl) acrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (23.93 mg; overall yield: 40.68%). The desired product has the following structure and characteristics.

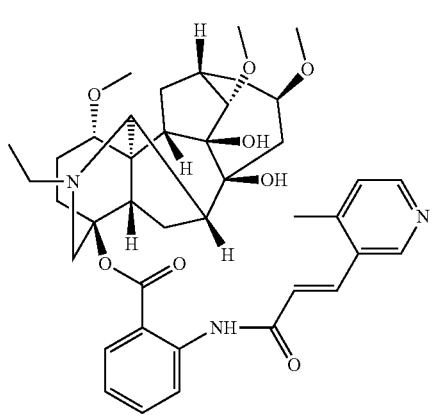

(6)

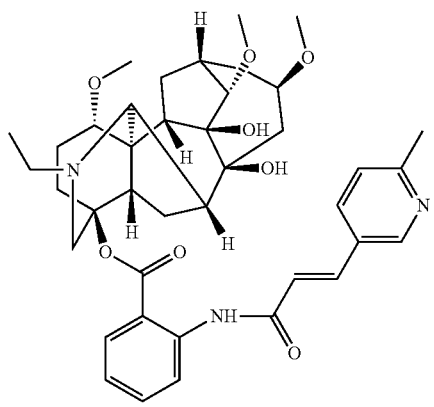

(7)

White crystalline powder. M.P. 182-184° C. ¹H-NMR (400 MHz, DMSO-d$_6$) δ: 10.12 (1H, s), 8.48 (1H, s), 8.30 (4H, m), 7.99 (1H, d), 7.71 (1H, s), 6.97 (1H, d), 6.89 (1H, s), 3.65 (2H, s), 3.30 (9H, s), 2.85 (1H, d), 2.78 (1H, q), 2.77 (1H, t), 2.75 (2H, s), 2.54 (2H, d), 2.50 (5H, s), 2.40 (2H, q), 2.36 (1H, m), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.02 (3H, t); ¹³C-NMR (100 MHz, DMSO-d$_6$) δ: 168.0, 167.1, 150.0, 145.8, 143.9, 140.3, 137.8, 133.1, 130.1, 126.7, 124.8, 124.2, 119.2, 115.4, 92.2, 88.6, 86.1, 84.5, 80.1, 77.2, 69.9, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.0, 19.2, 13.6; MS (ESI) for [M+H]⁺: 688.8.

White crystalline powder. M.P. 182-184° C. ¹H-NMR (400 MHz, DMSO-d$_6$) δ: 10.12 (1H, s), 8.32 (1H, s), 8.30 (4H, m), 7.71 (1H, s), 7.64 (1H, d), 7.13 (1H, d), 6.89 (1H, s), 3.65 (2H, s), 3.30 (9H, s), 2.85 (1H, d), 2.78 (1H, q), 2.77 (1H, t), 2.75 (2H, s), 2.54 (2H, d), 2.53 (3H, s), 2.50 (2H, s), 2.40 (2H, q), 2.36 (1H, m), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.02 (3H, t); ¹³C-NMR (100 MHz, DMSO-d$_6$) δ: 168.0, 167.1, 160.8, 149.6, 140.3, 136.6, 133.2, 132.9, 130.1, 128.6, 124.8, 124.2, 119.2, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.0, 23.9, 13.6; MS (ESI) for [M+H]⁺: 688.8.

Example 7

Lappaconitine and 3-(4-methyl-3-pyridyl) Acrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 18.64 mg of 3-(4-methyl-3-pyridyl) acrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (22.68 mg; overall yield: 38.56%). The desired product has the following structure and characteristics.

Example 8

Lappaconitine and 3-(5-ethyl-3-pyridyl) Acrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 20.08 mg of 3-(5-ethyl-3-pyridyl) acrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (25.13 mg; overall yield: 41.87%). The desired product has the following structure and characteristics.

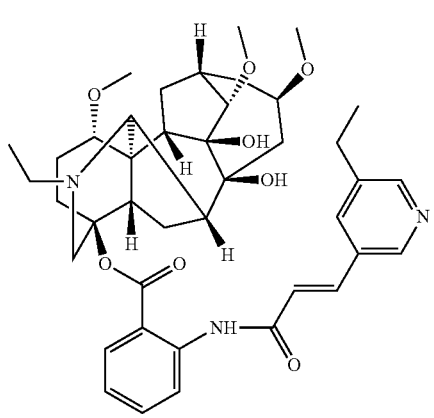

(8)

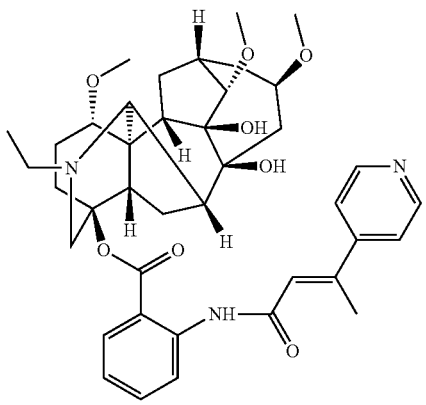

(9)

White crystalline powder. M.P. 182-184° C. $^1$H-NMR (400 MHz, DMSO-$d_6$) δ: 10.12 (1H, s), 8.82 (1H, s), 8.29 (1H, s), 8.00 (4H, m), 7.73 (1H, s), 7.71 (1H, s), 6.89 (1H, s), 3.65 (2H, s), 3.30 (9H, s), 2.85 (1H, d), 2.78 (1H, q), 2.77 (1H, t), 2.75 (2H, s), 2.73 (2H, q), 2.54 (2H, d), 2.50 (2H, s), 2.40 (2H, q), 2.36 (1H, m), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.25 (3H, t), 1.02 (3H, t); $^{13}$C-NMR (100 MHz, DMSO-$d_6$) δ: 168.0, 167.1, 150.8, 149.5, 140.3, 139.4, 136.6, 133.4, 130.1, 129.4, 124.8, 124.2, 119.2, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 26.3, 24.0, 14.5, 13.6; MS (ESI) for [M+H]$^+$: 702.4.

Example 9

Lappaconitine and 3-(4-pyridyl)-3-methacrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 18.64 mg of 3-(4-pyridyl)-3-methacrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (23.14 mg; overall yield: 39.34%). The desired product has the following structure and characteristics.

White crystalline powder. M.P. 182-184° C. $^1$H-NMR (400 MHz, DMSO-$d_6$) δ: 10.12 (1H, s), 8.54 (2H, d), 8.30 (4H, m), 7.47 (2H, d), 7.35 (1H, s), 7.19 (1H, s), 6.86 (1H, s), 3.65 (2H, s), 3.30 (9H, s), 2.85 (1H, d), 2.78 (1H, q), 2.77 (1H, t), 2.75 (2H, s), 2.54 (2H, d), 2.50 (2H, s), 2.40 (2H, q), 2.36 (1H, m), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.02 (3H, t); $^{13}$C-NMR (100 MHz, DMSO-$d_6$) δ: 167.1, 166.3, 153.9, 149.6, 144.3, 140.3, 133.2, 130.1, 125.4, 124.2, 123.0, 119.2, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.0, 13.6, 13.0; MS (ESI) for [M+H]$^+$: 688.8.

Example 10

Lappaconitine and 3-(4-pyridyl)-2-methacrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 18.64 mg of 3-(4-pyridyl)-2-methacrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (25.78 mg; overall yield: 43.83%). The desired product has the following structure and characteristics.

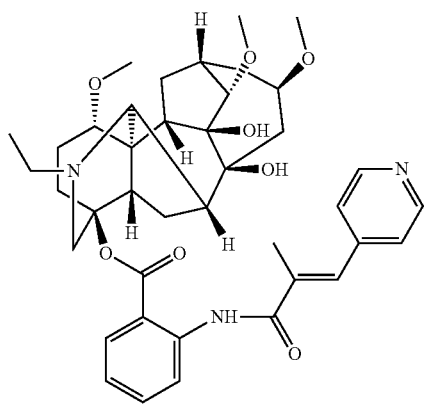

(10)

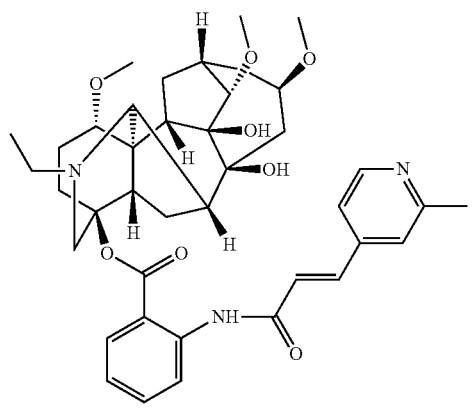

(11)

White crystalline powder. M.P. 182-184° C. $^1$H-NMR (400 MHz, DMSO-d$_6$) δ: 10.12 (1H, s), 8.61 (2H, d), 8.30 (4H, m), 7.40 (2H, d), 7.35 (1H, s), 7.24 (1H, s), 6.86 (1H, s), 3.65 (2H, s), 3.30 (9H, s), 2.85 (1H, d), 2.78 (1H, q), 2.77 (1H, t), 2.75 (2H, s), 2.54 (2H, d), 2.53 (3H, s), 2.50 (2H, s), 2.40 (2H, q), 2.36 (1H, m), 2.13 (4H, m), 1.99 (1H, t), 1.95 (2H, t), 1.88 (4H, m), 1.80 (2H, d), 1.73 (1H, t), 1.70 (4H, m), 1.52 (2H, d), 1.48 (1H, s), 1.45 (2H, q), 1.02 (3H, t); $^{13}$C-NMR (100 MHz, DMSO-d$_6$) δ: 167.1, 166.3, 153.9, 149.6, 144.5, 140.3, 137.9, 133.2, 130.1, 127.5, 124.2, 123.0, 119.2, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.0, 13.6, 13.0; MS (ESI) for [M+H]$^+$: 688.8.

White crystalline powder. M.P. 182-184° C. $^1$H-NMR (400 MHz, DMSO-d$_6$) δ: 10.12 (1H, s), 8.54 (2H, d), 8.30 (4H, m), 7.47 (2H, d), 7.35 (1H, s), 7.24 (1H, s), 6.86 (1H, s), 3.65 (2H, s), 3.30 (9H, s), 2.85 (1H, d), 2.78 (1H, q), 2.77 (1H, t), 2.75 (2H, s), 2.54 (2H, d), 2.50 (2H, s), 2.43 (3H, s), 2.40 (2H, q), 2.36 (1H, m), 2.13 (4H, m), 1.99 (1H, t), 1.95 (2H, t), 1.88 (4H, m), 1.80 (2H, d), 1.73 (1H, t), 1.70 (4H, m), 1.5 (2H, d), 1.48 (1H, s), 1.45 (2H, q), 1.02 (3H, t); $^{13}$C-NMR (100 MHz, DMSO-d$_6$) δ: 168.0, 167.1, 161.4, 148.9, 142.2, 141.4, 140.3, 133.2, 130.1, 125.4, 124.2, 119.2, 118.9115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.0, 13.6; MS (ESI) for [M+H]$^+$: 688.8.

Example 11

Lappaconitine and 3-(3-methyl-4-pyridyl) Acrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 18.64 mg of 3-(3-methyl-4-pyridyl) acrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (22.51 mg; overall yield: 38.27%). The desired product has the following structure and characteristics.

Example 12

Lappaconitine and 3-(3-ethyl-4-pyridyl) Acrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 20.08 mg of 3-(3-ethyl-4-pyridyl) acrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (26.11 mg; overall yield: 43.50%). The desired product has the following structure and characteristics.

(12)

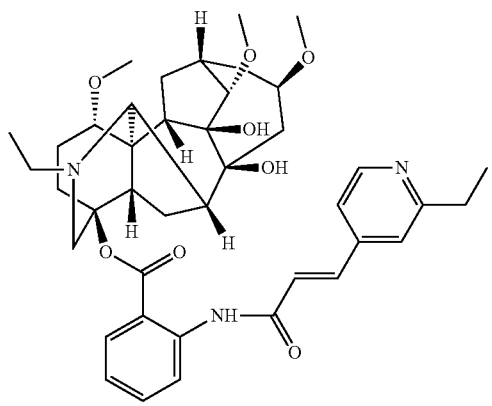

(13)

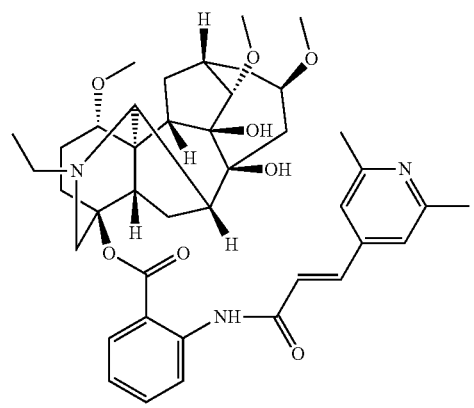

White crystalline powder. M.P. 182-184° C. $^1$H-NMR (400 MHz, DMSO-d$_6$) δ: 10.12 (1H, s), 8.54 (2H, d), 8.30 (4H, m), 7.47 (2H, d), 7.35 (1H, s), 7.24 (1H, s), 6.86 (1H, s), 3.65 (2H, s), 3.40 (2H, q), 3.30 (9H, s), 2.85 (1H, d), 2.78 (1H, q), 2.77 (1H, t), 2.75 (2H, s), 2.54 (2H, d), 2.50 (2H, s), 2.40 (2H, q), 2.36 (1H, m), 2.13 (4H, m), 1.99 (1H, t), 1.95 (2H, t), 1.88 (4H, m), 1.80 (2H, d), 1.73 (1H, t), 1.70 (4H, m), 1.50 (2H, d), 1.48 (1H, s), 1.45 (2H, q), 1.25 (3H, t), 1.02 (3H, t); $^{13}$C-NMR (100 MHz, DMSO-d$_6$) δ: 168.0, 167.1, 160.1, 148.6, 142.2, 141.4, 140.3, 133.2, 130.1, 125.4, 124.2, 119.2, 118.9, 117.5, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 30.9, 26.9, 26.4, 24.0, 13.6, 13.0; MS (ESI) for [M+H]$^+$: 702.4.

Example 13

Lappaconitine and 3-(3,5-dimethyl-4-pyridyl) Acrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 20.08 mg of 3-(3,5-dimethyl-4-pyridyl) acrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (34.09 mg; overall yield: 56.79%). The desired product has the following structure and characteristics.

White crystalline powder. M.P. 182-184° C. $^1$H-NMR (400 MHz, DMSO-d$_6$) δ: 10.12 (1H, s), 8.30 (4H, m), 7.35 (1H, s), 7.24 (2H, s), 7.19 (1H, s), 3.65 (2H, s), 3.30 (9H, s), 2.85 (1H, d), 2.78 (1H, q), 2.77 (1H, t), 2.75 (2H, s), 2.54 (2H, d), 2.53 (6H, t), 2.50 (2H, s), 2.40 (2H, q), 2.36 (1H, m), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.02 (3H, t); $^{13}$C-NMR (100 MHz, DMSO-d$_6$) δ: 168.0, 167.1, 157.9, 142.4, 141.4, 140.3, 133.2, 130.1, 125.4, 124.2, 119.2, 115.7, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.0, 20.4, 13.6; MS (ESI) for [M+H]$^+$: 702.8.

Example 14

Lappaconitine and 3-(5-methyl-2-pyridyl) Acrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 18.64 mg of 3-(5-methyl-2-pyridyl) acrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (35.22 mg; overall yield: 59.87%). The desired product has the following structure and characteristics.

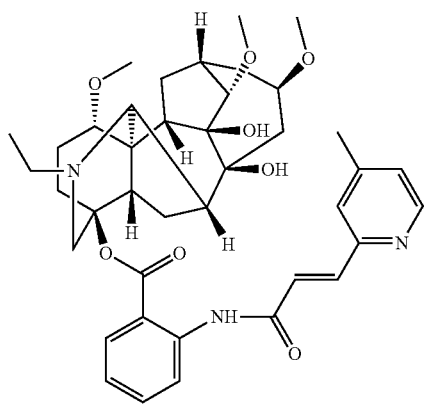

(14)

White crystalline powder. M.P. 182-184° C. $^1$H-NMR (400 MHz, DMSO-d$_6$) δ: 10.12 (1H, s), 8.46 (1H, d), 8.30 (4H, m), 7.76 (1H, s), 7.50 (1H, s), 7.39 (1H, s), 7.34 (1H, d), 3.65 (2H, s), 3.30 (9H, s), 2.85 (1H, d), 2.78 (1H, q), 2.77 (1H, t), 2.75 (2H, s), 2.54 (2H, d), 2.50 (2H, s), 2.40 (2H, q), 2.36 (4H, m), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.02 (3H, t); $^{13}$C-NMR (100 MHz, DMSO-d$_6$) δ: 168.0, 167.1, 155.2, 148.3, 147.0, 140.3, 138.2, 133.2, 130.1, 127.1, 124.5, 124.2, 119.2, 115.7, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.0, 21.7, 13.6; MS (ESI) for [M+H]$^+$: 688.8.

Example 15

Lappaconitine and 3-(5-ethyl-2-pyridyl) Acrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 20.08 mg of 3-(5-ethyl-2-pyridyl) acrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (33.70 mg; overall yield: 56.15%). The desired product has the following structure and characteristics.

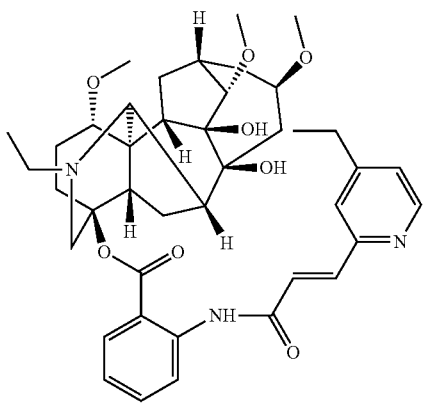

(15)

White crystalline powder. M.P. 182-184° C. $^1$H-NMR (400 MHz, DMSO-d6) δ: 10.12 (1H, s), 8.46 (1H, d), 8.30 (4H, m), 7.76 (1H, s), 7.50 (1H, s), 7.39 (1H, s), 7.34 (1H, d), 3.65 (2H, s), 3.30 (9H, s), 2.85 (1H, d), 2.78 (1H, q), 2.77 (1H, t), 2.75 (2H, s), 2.60 (2H, q), 2.54 (2H, d), 2.50 (2H, s), 2.40 (2H, q), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.25 (3H, t), 1.02 (3H, t); $^{13}$C-NMR (100 MHz, DMSO-d$_6$) δ: 167.1, 155.3, 154.6, 149.7, 146.4, 137.2, 133.8, 130.7, 126.0, 124.4, 122.5, 117.0, 113.4, 109.9, 91.7, 91.4, 84.5, 66.7, 61.0, 57.7, 57.4, 54.4, 50.8, 46.7, 45.5, 41.6, 40.3, 37.5, 37.3, 32.3, 28.6, 27.8, 27.2, 26.1, 14.5, 14.4, 13.3; MS (ESI) for [M+H]$^+$: 702.8.

Example 16

Lappaconitine and 3-(3,5-dimethyl-2-pyridyl) Acrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 20.08 mg of 3-(3,5-dimethyl-2-pyridyl) acrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (33.07 mg; overall yield: 51.15%). The desired product has the following structure and characteristics.

(16)

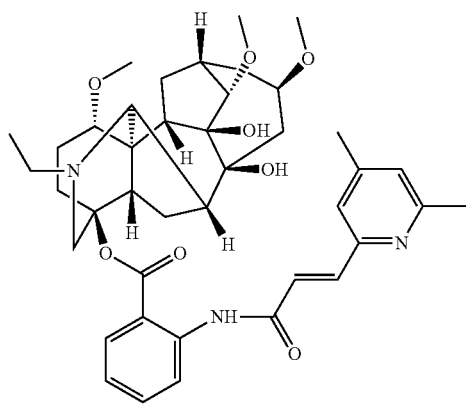

White crystalline powder. M.P. 182-184° C. $^1$H-NMR (400 MHz, DMSO-$d_6$) δ: 10.12 (1H, s), 7.76 (1H, s), 8.30 (4H, m), 7.50 (1H, s), 7.28 (1H, s), 7.23 (1H, s), 3.65 (2H, s), 3.30 (9H, s), 2.85 (1H, d), 2.78 (1H, q), 2.77 (1H, t), 2.75 (2H, s), 2.54 (2H, d), 2.53 (3H, s), 2.50 (2H, s), 2.40 (2H, q), 2.36 (4H, m), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.02 (3H, t); $^{13}$C-NMR (100 MHz, DMSO-$d_6$) δ: 168.0, 167.1, 158.3, 154.8, 146.6, 140.3, 138.2, 133.2, 130.1, 124.5, 124.2, 123.6, 122.6, 119.2, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.0, 22.0, 20.4, 13.6; MS (ESI) for [M+H]$^+$: 702.8.

Example 17

Lappaconitine and 3-(5-isopropyl-2-pyridyl) Acrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 21.52 mg of 3-(5-isopropyl-2-pyridyl) acrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (27.99 mg; overall yield: 46.63%). The desired product has the following structure and characteristics.

(17)

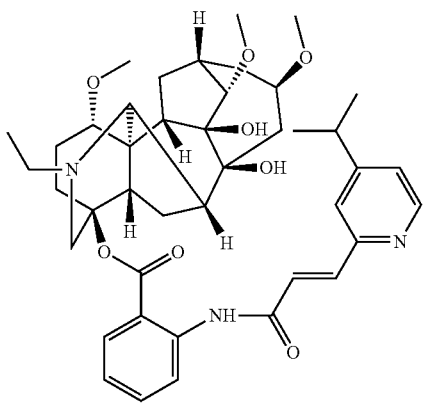

White crystalline powder. M.P. 182-184° C. $^1$H-NMR (400 MHz, DMSO-$d_6$) δ: 10.12 (1H, s), 8.46 (1H, s), 7.76 (1H, s), 7.30 (4H, m), 7.50 (1H, s), 7.39 (1H, s), 7.34 (1H, d), 3.65 (2H, s), 3.30 (9H, s), 2.87 (1H, m), 2.85 (1H, d), 2.78 (1H, q), 2.77 (1H, t), 2.75 (2H, s), 2.54 (2H, d), 2.50 (2H, s), 2.40 (2H, q), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.20 (6H, t), 1.02 (3H, t); $^{13}$C-NMR (100 MHz, DMSO-$d_6$) δ: 168.0, 167.1, 158.1, 155.1, 146.9, 140.3, 138.2, 133.2, 130.1, 124.5, 124.2, 123.0, 119.2, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 33.6, 31.9, 26.9, 26.4, 24.0, 23.3, 13.6; MS (ESI) for [M+H]$^+$: 716.8.

Example 18

Lappaconitine and 3-(3-methyl-2-pyridyl)-2-methacrylic Acid 50 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 20.08 mg of 3-(3-methyl-2-pyridyl)-2-methacrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (24.87 mg; overall yield: 41.43%). The desired product has the following structure and characteristics.

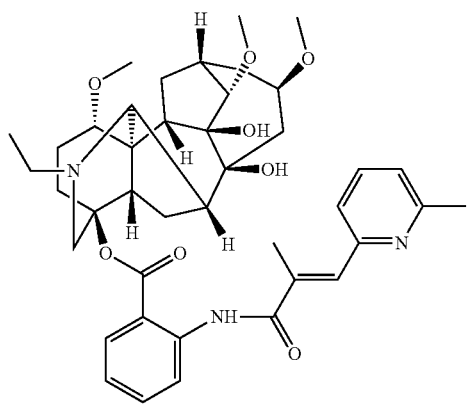 (18)

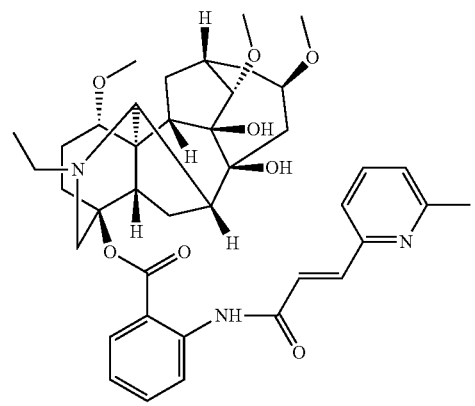 (19)

White crystalline powder. M.P. 182-184° C. ¹H-NMR (400 MHz, DMSO-d₆) δ: 10.12 (1H, s), 8.30 (4H, m), 7.55 (1H, d), 7.48 (1H, s), 7.27 (1H, d), 3.65 (2H, s), 3.30 (9H, s), 2.85 (1H, d), 2.78 (1H, q), 2.77 (1H, t), 2.75 (2H, s), 2.54 (2H, d), 2.53 (3H, s), 2.50 (2H, s), 2.43 (1H, s), 2.40 (2H, q), 2.36 (1H, m), 2.13 (4H, m), 1.99 (1H, t), 1.95 (2H, t), 1.88 (4H, m), 1.80 (2H, d), 1.73 (1H, t), 1.70 (4H, m), 1.55 (H, d), 1.48 (1H, s), 1.45 (2H, q), 1.02 (3H, t); 13C-NMR (100 MHz, DMSO-d₆) δ: 167.1, 163.8, 157.8, 154.3, 140.3, 137.2, 133.2, 131.0, 126.6, 124.2, 122.9, 121.3, 19.2, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.3, 24.0, 11.9, 13.6; MS (ESI) for [M+H]+: 702.3.

Example 19

Lappaconitine and 3-(3-methyl-2-pyridyl) Acrylic Acid 0 mg of lappaconitine and 5 mL ethanol were added to a 25 mL reaction flask. An appropriate amount of 2% HCl was added to the reaction mixture, and the reaction mixture was stirred at room temperature. The reaction was monitored with TLC until completion. After reaction is complete, reaction solvent was removed at 50° C. under vacuum to obtain an intermediate. The intermediate was then dissolved in DMF, and 18.64 mg of 3-(3-methyl-2-pyridyl) acrylic acid and catalytic amount of DCC were added to the DMF solution. The mixture was then stirred and heated at 70° C. After TLC showed the reaction was complete, water was added to the mixture to quench the reaction. The reaction mixture was extracted with DCM. DCM solution was then concentrated, and fresh column chromatography yielded the desired product as a white crystalline powder (31.70 mg; overall yield: 53.89%). The desired product has the following structure and characteristics.

White crystalline powder. M.P. 182-184° C.; ¹H-NMR (400 MHz, DMSO-d₆) δ: 10.12 (1H, s), 8.30 (4H, m), 7.76 (1H, s), 7.55 (1H, d), 7.51 (1H, t), 7.50 (1H, s), 7.27 (1H, d), 3.65 (2H, s), 3.30 (9H, s), 2.85 (1H, d), 2.78 (1H, q), 2.77 (1H, t), 2.75 (2H, s), 2.54 (2H, d), 2.53 (3H, s), 2.50 (2H, s), 2.40 (2H, q), 2.36 (1H, m), 2.13 (4H, m), 1.99 (1H, t), 1.95 (2H, t), 1.88 (4H, m), 1.80 (2H, d), 1.73 (1H, t), 1.70 (4H, m), 1.55 (2H, d), 1.48 (1H, s), 1.45 (2H, q), 1.02 (3H, t); ¹³C-NMR (100 MHz, DMSO-d₆) δ: 168.0, 167.1, 157.8, 154.3, 140.3, 138.2, 137.2, 133.2, 130.1, 124.5, 124.2, 122.9, 121.3, 119.2, 115.4, 92.2, 88.6, 86.1, 84.5, 80.1, 77.2, 69.9, 58.5, 58.0, 57.7, 57.4, 51.0, 48.6, 47.6, 44.9, 42.9, 41.6, 31.9, 26.9, 26.4, 24.3, 24.0, 13.6; MS (ESI) for [M+H]+: 688.8.

Example 20

The anti-tumor activity test of the compounds of the present invention

The compounds of the present invention were subjected to tumor cell proliferation inhibition test, and the conventional MTT method was used as the test method.

Cell lines selected are human prostate cancer cell line (PC-3), human gastric adenocarcinoma cell line (SGC-7901), and human lung cancer cell (A-549). The culture medium was DMEM+15% NBS+double antibody.

Preparation of the sample solutions: compounds were dissolved in DMSO (Merck), and PBS (−) was add to 100 µL of the solution or homogeneous suspension. The solution or suspension was diluted with DMSO and PBS(−) to final concentrations of 0.1, 1, 10, 20, 40, 60, 80, 100 µmol/L.

Anti-tumor agent 5-fluorouracil (5-FU) was used as control and was prepared in the same way as the compounds.

Experimental Principle:

Living cells mitochondria in the dehydrogenase can reduce yellow MTT to water-insoluble blue-violet product MT (MTT formazan), deposited in the cells. The amount of production is proportional to the number of living cells. Dead cells do not reduce yellow MTT. DMSO can dissolve blue violet crystals, and the color depth is proportional to the amount contained, so the absorbance measured by the microplate reader can reflect the cell viability.

Methods:

The exponential phase cells were digested and counted and seeded in 96-well plates at a density of 2×104/mL at 100 µl per well. After 24 hours of incubation, the cells to be tested were treated with 0.1, 1, 10, 20, 40, 60, 80, 100 µmol/L of the compounds. Each experimental group had 5 wells in each concentration, and the culture medium containing 0.4% DMSO was used as control. After 48 hours, the supernatant was discarded, and 100 μl of MTT ((2-(4,5-dimethyl-2-thiazolyl)-3,5-diphenyl-2H-tetrazole hydrobromide) (1 mg/mL) was added to each well. After another 4 hours, the supernatant was discarded, and 100 μL of DMSO was added to each well. After mixing, the absorbance was measured at 570 nm using a microplate reader. An $IC_{50}$ calculation software was used to determine the half inhibitory concentration ($IC_{50}$).

The test results are shown in Table 1. The compounds listed in the table correspond to the compounds described above.

TABLE 1

Half Inhibitory Concentration of Compounds on Differen Tumor Cells $IC_{50}$ (unit: μmol/L)

| Compd. | $IC_{50}$ (μmol/L) | | |
|---|---|---|---|
| | PC-3 | A549 | SGC-7901 |
| 1 | 18.10 ± 0.64 | 9.12 ± 2.53 | 22.46 ± 1.35 |
| 2 | 26.40 ± 0.36 | 13.36 ± 2.78 | 26.34 ± 0.37 |
| 3 | 15.21 ± 1.18 | 38.51. ± 1.73 | 13.65 ± 1.28 |
| 4 | >100 | 67.31 ± 0.44 | >100 |
| 5 | 11.29 ± 0.64 | 13.17 ± 0.39 | 29.62 ± 3.54 |
| 6 | 33.54 ± 1.17 | 42.65 ± 0.38 | 37.81 ± 0.42 |
| 7 | 43.32 ± 1.42 | 47.31 ± 0.44 | 39.31 ± 1.74 |
| 8 | 38.10 ± 0.44 | 25.12 ± 2.23 | 33.47 ± 1.18 |
| 9 | 73.37 ± 0.69 | >100 | >100 |
| 10 | >100 | >100 | >100 |
| 11 | 10.20 ± 0.78 | 18.56 ± 0.43 | 10.23 ± 0.45 |
| 12 | 13.86 ± 0.10 | 21.68 ± 0.45 | 25.05 ± 0.16 |
| 13 | 16.63 ± 1.87 | 32.31 ± 1.34 | 18.02 ± 0.58 |
| 14 | 67.82 ± 1.30 | 41.32 ± 1.42 | 87.02 ± 0.58 |
| 15 | 44.12 ± 2.73 | 47.34 ± 2.56 | 21.78 ± 1.20 |
| 16 | 40.84 ± 2.55 | 69.32 ± 1.42 | >100 |
| 17 | 61.31 ± 1.24 | >100 | >100 |
| 18 | >100 | >100 | >100 |
| 19 | >100 | >100 | 95.12 ± 1.92 |
| 5-FU | 8.17 ± 0.39 | 15.62 ± 3.54 | 22.44 ± 1.67 |

The results show that compounds 1-19 have different degrees of antitumor activities in the tested three cell lines. Compounds 11, 12 and 5 exhibit inhibitory effect on the cells, and have equal or better activities than 5-fluorouracil in the 3 cell lines tested. In summary, these compounds can be used in cancer research and to treat various cancers.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A lappaconitine aza-cinnamic acid derivative selected from the group consisting of

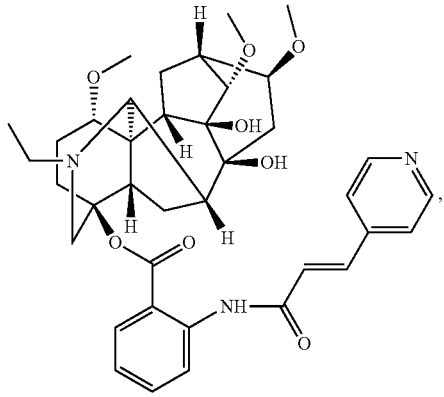

(1)

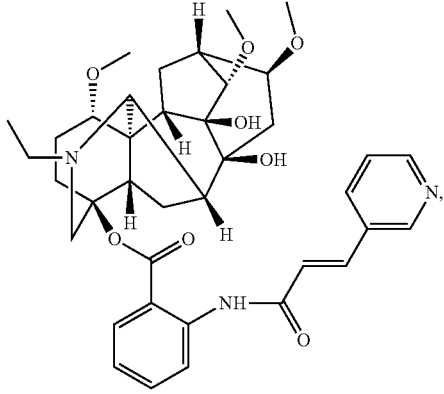

(2)

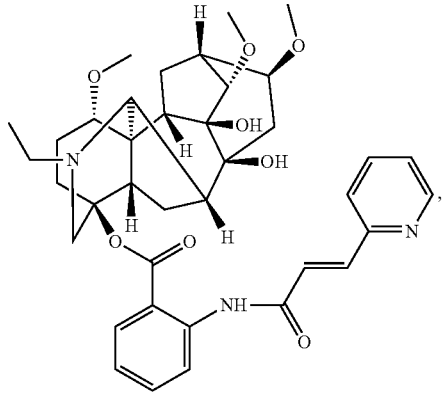

(3)

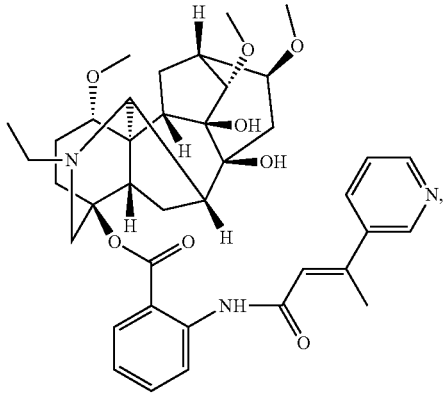

(4)

-continued
(5)
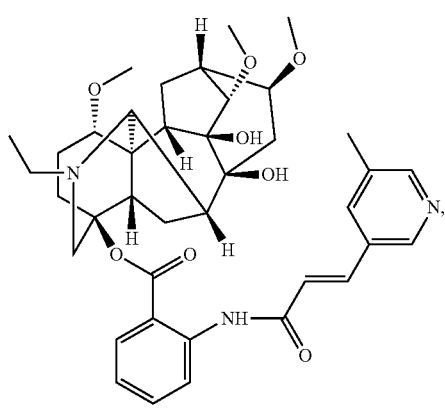
(6)
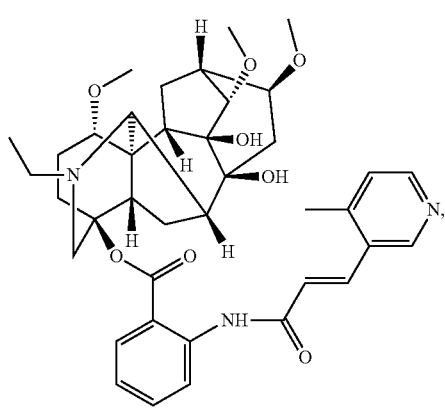
(7)
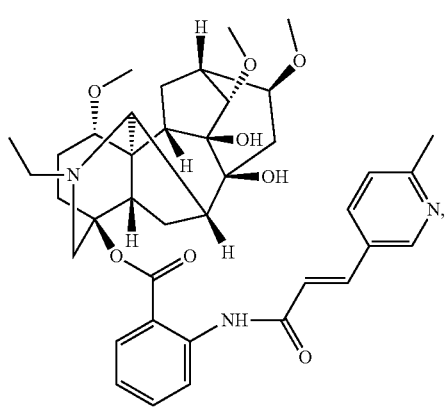
(8)
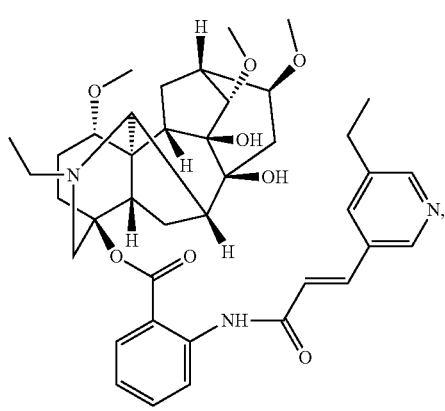
-continued
(9)
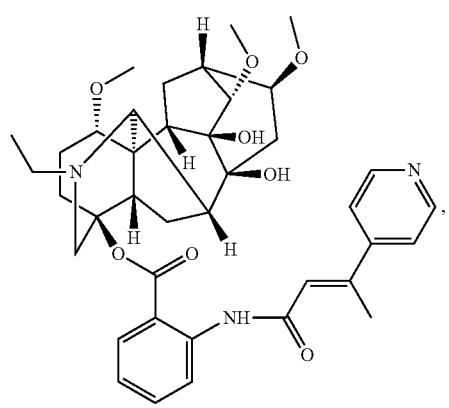
(10)
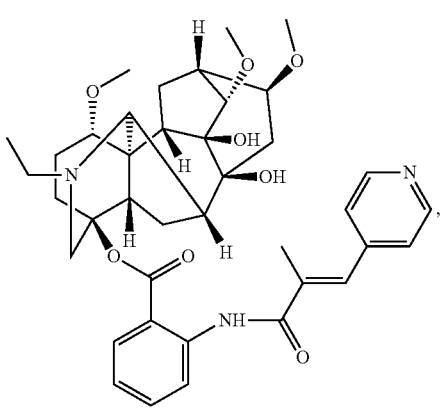
(11)
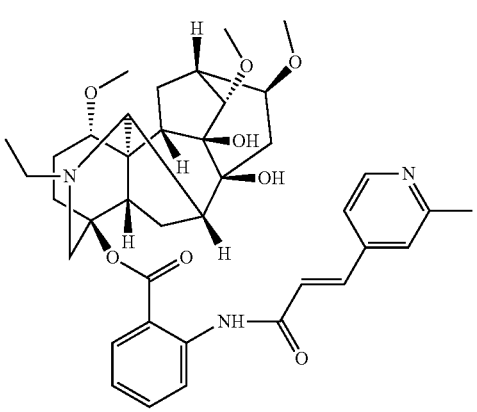
(12)
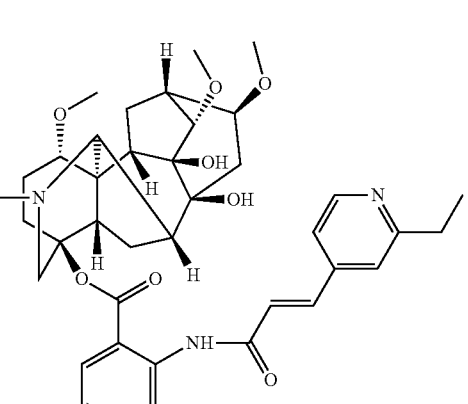

-continued
(13)
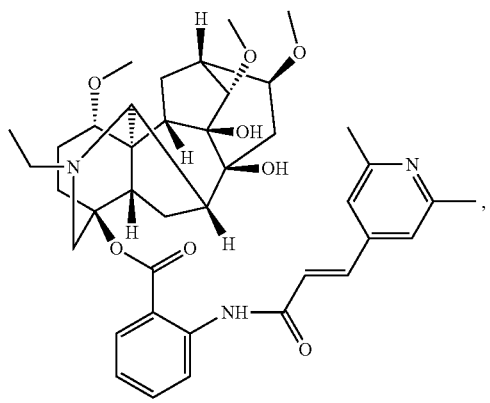
(14)
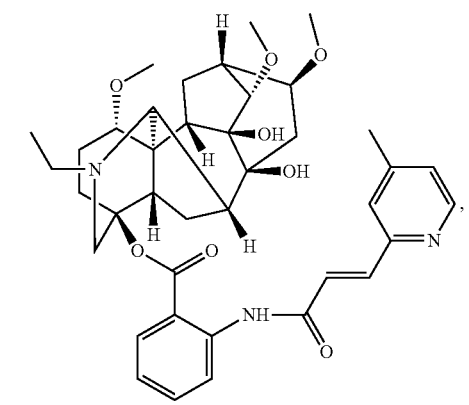
(15)
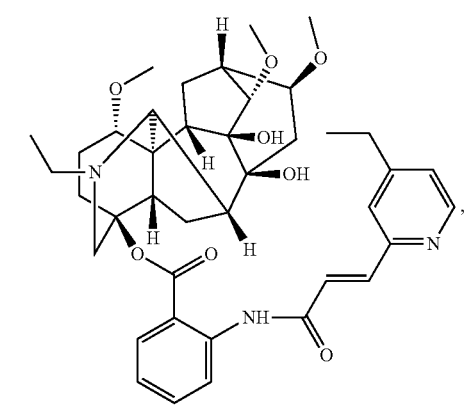
(16)
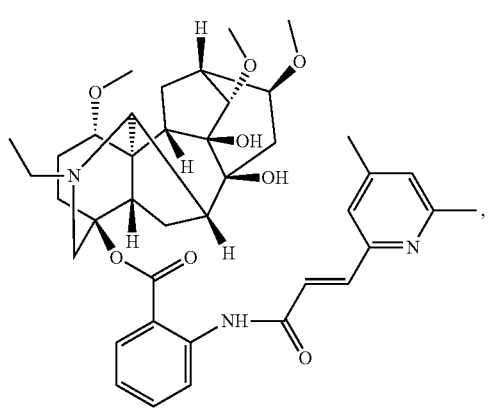
-continued
(17)
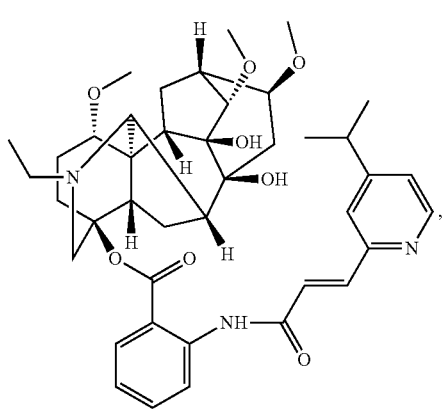
(18)
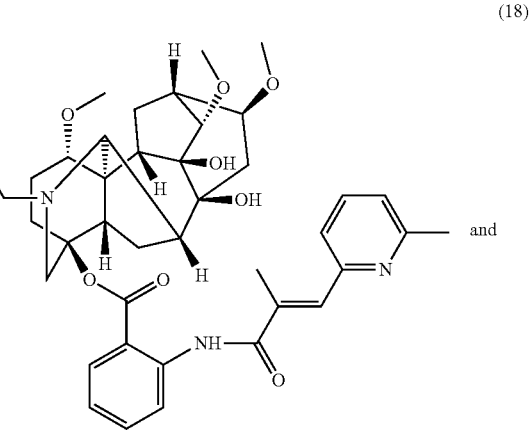
and
(19)
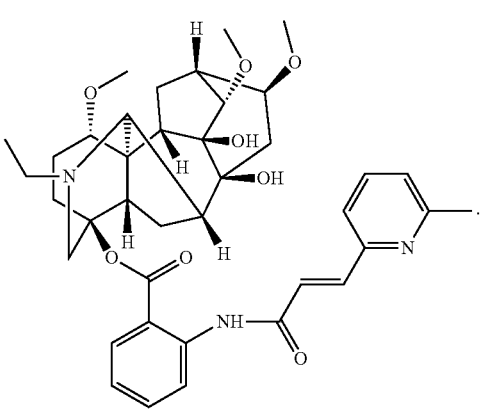
2. A method of preparing lappaconitine Aza-cinnamic acid derivatives with antitumor activities comprising:

reacting a compound of formula (II):

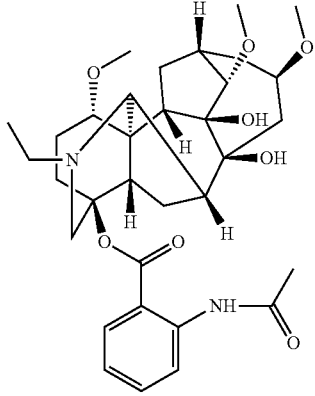

(II)

with HCl to obtain a compound of formula (III):

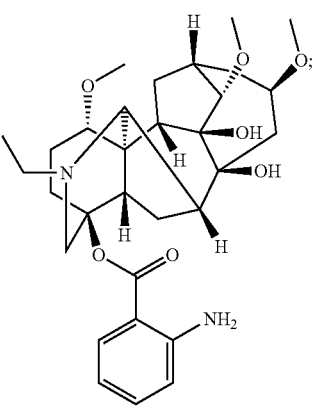

(III)

and reacting the compound of formula (III) with a compound of formula (IV):

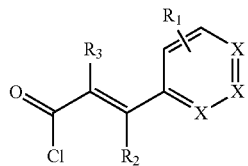

(IV)

to obtain a lappaconitine aza-cinnamic acid derivative having the following formula (I):

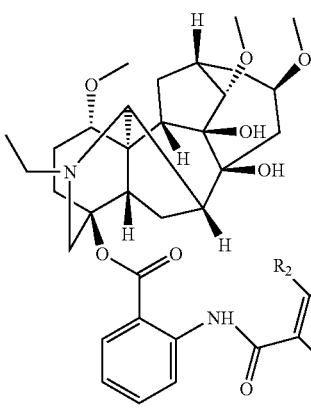

(I)

wherein X is C or N, and $R_1$, $R_2$, and $R_3$ are independently H or lower alkyl.

3. The method of claim 2, wherein the compound of formula (II) reacts with 2% HCl in ethanol in a molar ratio of 1:5.

4. The method of claim 2, wherein the compound of formula (III) reacts with the compound of formula (IV) in DMF in a molar ratio of 1:1.1-12 with DCC as a catalyst.

5. The method of claim 4, wherein the compound of formula (III) reacts with the compound of formula (IV) at 50° C.-90° C.

6. The method of claim 4, wherein the compound of formula (III) reacts with the compound of formula (IV) at 60° C.-80° C.

* * * * *